June 1, 1965 A. P. HOWARD Plant Pat. 2,524
ROSE PLANT
Filed Nov. 4, 1963
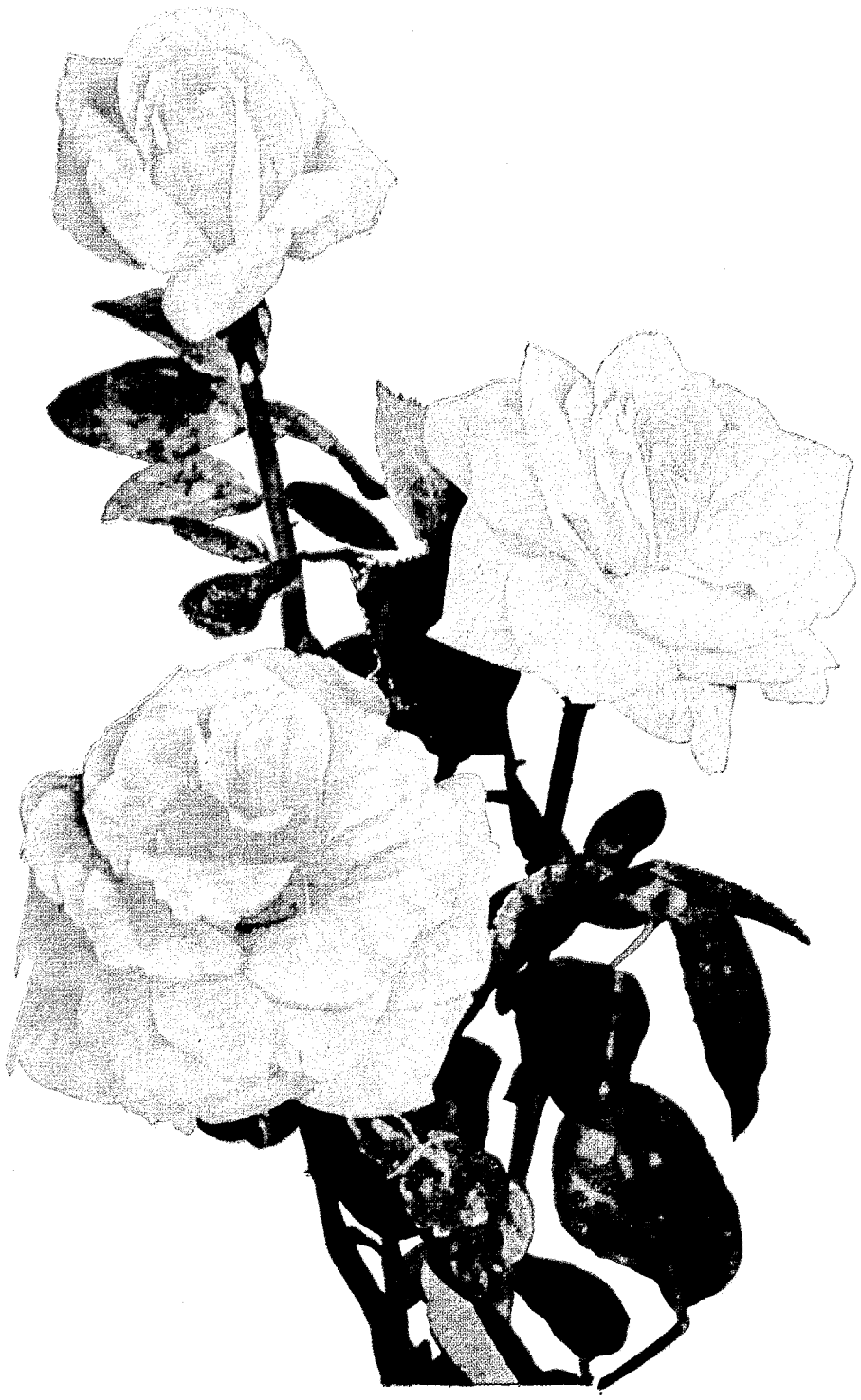
INVENTOR
ARTHUR P. HOWARD
BY J. F. Cunco
ATTORNEY United States Patent Office Plant Pat. 2,524
Patented June 1, 1965

2,524
ROSE PLANT

Arthur P. Howard, Sierra Madre, Calif., assignor to Great Western Rose Company, Inc., Pomona, Calif., a corporation of California Filed Nov. 4, 1963, Ser. No. 327,861
1 Claim. (Cl. Plt.—11)

This invention relates to a new and distinct variety of rose plant which falls in the hybrid tea class.

The plant resulted from cross-breeding Louis Phillippe, an unpatented variety, with The Doctor, also an unpatented variety, after numerous experiments conducted by me in Montebello, county of Los Angeles, State of California. The original plant was produced by me in 1955, the seed parent was Louis Phillippe and the pollen parent was The Doctor.

This new variety of rose plant is unique in that the rose has very long stems and when a stem is cut a new stem takes off from the side of the stem that was cut and forms another long stem. This rose is further distinguished from other varieties in that the flowers are a bright orange scarlet and also have a coppery tinge. The flowers are produced in abundance during the growing season that normally extends from April through December.

In comparing the blooms of my novel variety with those of its seed parent Louis Phillippe, the flowers are found to be a coppery tinged orange-scarlet whereas the flowers of Louis Phillippe are a deep purplish scarlet red; the unusual property of growing a new stem from the side of one that has been cut from the plant is not found in the seed parent. Compared to its pollen parent The Doctor the flower does not resemble the clear rose pink blooms of the pollen parent; the pollen parent also does not exhibit the unusual property of growing a new stem at the side of one that was cut. The new variety also produces the flowers on longer stems than those of its pollen parent. The new variety also grows to a greater height than either of its parent plants and may reach a height of seven feet.

The new rose belongs to the outdoor bush type and is used principally for cut flowers and for garden ornamentation. The plant has been produced asexually by budding performed at Montebello, California. The plant and flowers reproduce true with all their distinguishing characteristics, and these distinguishing features are transmitted through succeeding propagations of the variety. The plant will not reproduce true from seed.

The accompanying illustrations in color show a typical specimen of the flower and foliage. The colors are as correct as it is possible to reproduce them by the type of color representation employed.

A detailed description of the new variety of rose follows, and to facilitate identification of the important colors described in the specification, the designations adopted by the British Horticultural Colour Charts have been followed.

This new rose variety belongs to the outdoor bush type and is of the so-called hybrid tea class. Its coppery bright orange scarlet blooms make it particularly desirable for cut flowers and impart considerable color to any garden or landscape.

*The flower*

Locality where grown and observed: Montebello, California; Temple City, California; and La Puente, California.

Flowers Borne: Singly on stems approximately eighteen inches in length.

Number of blooms: When grown outdoors the plant produces an abundant number of blooms, the plant usually carries about twenty-five blooms.

Continuity: The plant blooms continuously from the first of April through December in the coastal portion of southern California.

Fragrance: The flowers have a very good tea fragrance.

Bud:

*Peduncle.*—Length—average length is 3½"; caliper is average. Color—olive green with a definite dark bronze tone.

*Before calyx breaks.*—Size—usually about ¾" across. Form—medium length and conical.

*As calyx breaks.*—Color—scarlet orange to orange. Sepals—almond shaped measuring one inch by one-quarter inch.

*As first petal opens.*—Size—approximately two by one and three quarters inches; some petals may be as much as two and one half inches long, with a width to correspond. Color—tip and outer rim—Porcelain Rose 620; center—Barium Yellow 503. Form—cuneate with a good aspect; margin is entire. Opening—there is a tendency for the flower to open more quickly on a hot day.

Bloom:

*Size.*—Averages between four to four and one half inches when fully opened.

*Petalage.*—Number of petals varies between thirty-five and forty-five, arranged regularly.

*Form.*—High centered, robust and globular when first fully opened, the inner petals being somewhat smaller than the outer petals.

*Petals.*—Texture—velvety. Shape — cuneate with edges entire and exhibiting no reflex tendency.

(This description of a newly opened flower was taken from observations made on a rose grown in Temple City, California, in the month of October.)

*Color.*—Tip—Porcelain Rose 620/1. Center and base—Barium Yellow 503/1. The above colors are representative of all petals in the fully developed bloom. There is a predominant coppery tone to all of the petals.

The flower has the general characteristics set forth herein:

*General color effect.*—Between Porcelain Rose 620/1 and Barium Yellow 503/1.

*Behavior.*—Petals drop off clean. In normal climatic conditions the flower does not show any change but under unusual heat conditions the colors tend to diminish in intensity.

*Flower longevity.*—Flowers will last from 7 to 9 days on the bush; after having been cut the flowers will last about five days on the average.

*Reproductive organs*

Stamens: Average number of stamens is approximately thirty.

Filaments: Filaments are approximately ⅜" in length. Color—old gold.

Anthers: Anthers are prominent. Color—golden yellow.

Pollen: Moderate quantity. Color—golden yellow.

Pistils: Pistils are numerous.

Styles: Not prominent.

Stigma: Not prominent.

Ovaries: Ovaries are usually enclosed in the calyx.

Hips:

*Length.*—Average length.

*Form.*—Ovoid generally, approximately ⅜" by ⅜".

*Color.*—Dark green outside, somewhat lighter inside.

Seeds: The seeds are of average size but do not set freely.

*The plant*

Foliage:

*Leaves.*—Compound of an average of five leaflets; normal in quantity. Leathery and glossy with the margins very slightly serrate. Shape—ovate in shape. Size—about 1¾″ to 2″ in length, and 1¼″ to 1½″ in width. Color—Parsley Green oo962/3 on upper side; Willow Green ooo862/1 on underside.

*Leaflets.*—Shape—ovoid with apex slightly acute. Margins are slightly serrate. Color—mature leaves—upper side is Parsley Green oo962/3, with the lower side of leaflet Willow Green ooo826/1; young leaves—have approximately the same color as mature leaves but have a pronounced reddish cast. Type—imparipinnate. Stipules — prominent, being about ¾″ long.

Growth:

*Habit.*—Upright and well branched. Plant grows from five to seven feet in height. Excellent productivity with hardy and vigorous growth.

*Canes.*—½″ to ¾″ in diameter after plant is fully established.

*Main stems.*—Some stems reach a length of 36″. Color — bronze green. Prickles — approximately ¼″ in length and widely spaced; slightly reclining; very few on stem; color—dull rose; hair—none. Small prickles—none.

*Branches.*—Color—bronze green. Shape—predominantly vertical. Hair—none. Small prickles—none.

*New shoots.*—Color—same as mature growth but more maroon. Large prickles—scarcely noticeable. Small prickles—none.

Having described my invention, I claim:

The new and distinct variety of rose plant of the class designated as hybrid tea roses, substantially as herein shown and described, characterized particularly as to novelty by the distinctive rose-yellow flowers with a pronounced coppery tone, borne singly on long stems, the good fragrance of the flowers, the unique property of the plant in growing a new stem to replace one that was cut off, the new stem starting from the side of the stem at a point immediately below the point where the stem was cut and continuing in the direction of the former stem, the unusual height that the plant reaches, the abundance of flowers throughout the unusually long growing season, and the prolonged longevity of the flowers after they are cut.

No references cited.

ABRAHAM G. STONE, *Primary Examiner.*